(12) United States Patent
Kobal et al.

(10) Patent No.: US 10,335,378 B2
(45) Date of Patent: Jul. 2, 2019

(54) INHIBITION OF CENTRAL NERVOUS SYSTEM EFFECTS FROM SMOKING AND SENSORY EFFECTS FROM SMOKING

(71) Applicant: Altria Client Services LLC, Richmond, VA (US)

(72) Inventors: Gerd Kobal, Sandy Hook, VA (US); Justin Heynekamp, Glen Allen, VA (US); Peter Reeh, Erlangen (DE); Munmaya K. Mishra, Manakin Sabot, VA (US); Tetyana Kichko, Erlangen (DE)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 14/208,619

(22) Filed: Mar. 13, 2014

(65) Prior Publication Data

US 2014/0271733 A1 Sep. 18, 2014

Related U.S. Application Data

(60) Provisional application No. 61/799,102, filed on Mar. 15, 2013.

(51) Int. Cl.
| | |
|---|---|
| *A61P 25/34* | (2006.01) |
| *A61K 31/125* | (2006.01) |
| *A61K 31/045* | (2006.01) |
| *A61K 45/06* | (2006.01) |
| *A61K 31/22* | (2006.01) |
| *A61K 9/00* | (2006.01) |

(52) U.S. Cl.
CPC .......... *A61K 31/125* (2013.01); *A61K 31/045* (2013.01); *A61K 31/22* (2013.01); *A61K 45/06* (2013.01)

(58) Field of Classification Search
None
See application file for complete search history.

(56) References Cited

U.S. PATENT DOCUMENTS

| | | |
|---|---|---|
| 4,931,475 A | 6/1990 | Uji |
| 4,959,380 A | 9/1990 | Wilson |
| 5,298,257 A | 3/1994 | Bannon et al. |
| 5,643,905 A | 7/1997 | Moormann |
| 6,548,510 B1 | 4/2003 | Asmussen et al. |
| 6,682,757 B1 | 1/2004 | Wright |
| 6,750,291 B2 | 6/2004 | Kim et al. |
| 2005/0119309 A1* | 6/2005 | Papke et al. .......... 514/327 |
| 2012/0052021 A1* | 3/2012 | Kobal ........... A24B 15/30 424/48 |

FOREIGN PATENT DOCUMENTS

| | | |
|---|---|---|
| CN | 1269176 | 10/2000 |
| CN | 1557457 | 12/2004 |
| CN | 101181607 | 5/2008 |
| CN | 102266125 | 12/2011 |
| WO | WO 88/08304 | 11/1988 |
| WO | WO 0158436 A1 * | 8/2001 |
| WO | WO 2013/090410 | 6/2013 |

OTHER PUBLICATIONS

SIMONSEN, The Terpenes vol. II The Dicyclic Terpenes, Sesquiterpenes and their Derivatives, p. 291, 1932.*
Kichko et al., *Irritant? Induced CGRP Release from the Isolated Mouse Trachea and role of TRP Channels*, 189 (Supplement 653), Acta Physiologica, abstract, (2007).
Park et al., *Noncompetitive inhibition by camphor of nicotine acetylcholine receptors*, 61 Biochemical Pharmacology 787-793 (2001).
Quit Smoking Hub, http://www.quitsmokinghub.com/finally_free_product_facts.shtm printed on Apr. 10, 2007.
*Health Effects of Smokeless Tobacco Products Preliminary Report*, Scientific Committee on Emerging and Newly Identified Health Risks 1-146 (European Commission Jun. 21, 2007).
Wellcene Health, Nicobrevin, http://wellcene.co.uk/cgi-bin/loadpage.cgi?user_id=894&file+w-nicobrevin.html printed on Apr. 10, 2007.
International Search Report dated Jul. 21, 2014, issued in PCT/US2014/030984.

* cited by examiner

*Primary Examiner* — Robert T. Crow
*Assistant Examiner* — John P Nguyen
(74) *Attorney, Agent, or Firm* — Buchanan Ingersoll & Rooney PC

(57) ABSTRACT

Pharmaceutical compositions and methods of use therefor for reducing the desire to engage in smoking are disclosed. More specifically, the pharmaceutical composition utilizes an active ingredient to reduce the side effects of smoking cessation and to limit the molecular feedback caused by nicotine-mediated activation of acetylcholine receptors.

5 Claims, 12 Drawing Sheets

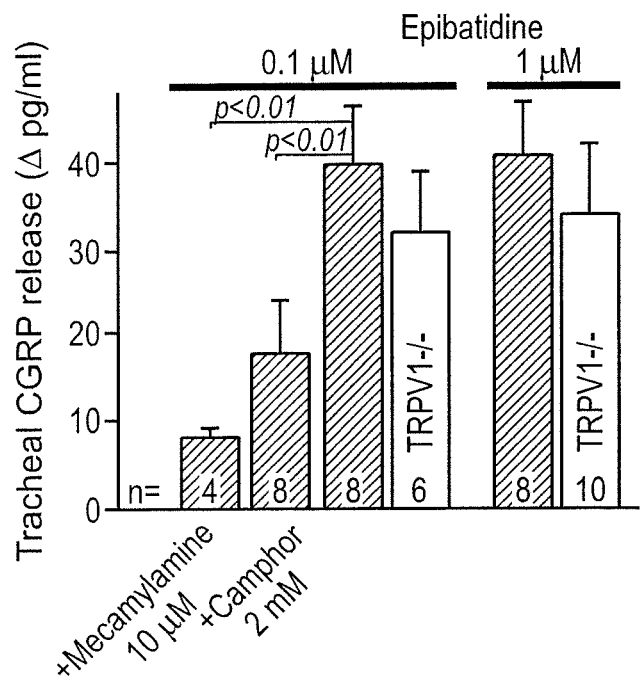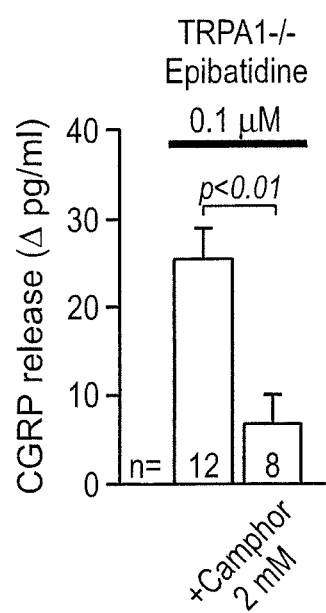

INHIBITION OF CENTRAL NERVOUS SYSTEM EFFECTS FROM SMOKING AND SENSORY EFFECTS FROM SMOKING

CROSS-REFERENCE TO RELATED APPLICATIONS

This application claims priority to U.S. Provisional Patent Application Ser. No. 61/799,102, filed on Mar. 15, 2013, which is incorporated herein by reference in its entirety for all purposes.

BACKGROUND

Acetylcholine receptors are found on the surface of many cells of the body, including nerve cells. There are two classes of nerve cells—those that make up the peripheral nervous system and those that make up the central nervous system. It is known that nicotine (in the brain) binds to acetylcholine receptors on nerve cells in the central nervous system to cause the release of neurotransmitters.

Various approaches have been taken to reduce an individual's desire to smoke tobacco products. Some of these methods target the nicotinic acetylcholine receptors responsible for transmitting signals to the brain when they react with nicotine. One previous approach to a pharmaceutical composition containing an active ingredient for decreasing an individual's desire to smoke resulted in the development of the drug product manufactured under the CHANTIX brand. CHANTIX, or varenicline, is a prescription medication that stimulates nicotine receptors more weakly than nicotine does. That is, it is a nicotinic receptor partial agonist. As a partial agonist it reduces nicotine-mediated cravings and decreases the pleasurable effects of cigarettes and other tobacco products, both of which may be beneficial to patients seeking to quit smoking. However, like many other commercially available products, CHANTIX does little to diminish the negative side effects associated with smoking cessation.

Thus, there remains a long-felt, yet currently unmet, need in the art to provide a product capable of reducing an individual's desire to smoke that also reduces the withdrawal symptoms associated with smoking cessation. The pharmaceutical composition disclosed herein describes a new use of a previously known and well-characterized active agent that operates to decrease withdrawal symptoms associated with smoking cessation. The pharmaceutical composition described herein also shows remarkable and unexpected efficacy as a pharmaceutical formulation for reducing an individual's desire to smoke.

BRIEF SUMMARY

A product for reducing an individual's desire to engage in smoking is disclosed, wherein the product comprises an effective amount of an active ingredient comprising at least one compound selected from the group consisting of camphor, isoborneol, bornyl acetate, isobornyl acetate, mono-bornyl succinate, mono-isobornyl succinate, mono-bornyl formate, and mono-isobornyl formate; wherein the product is free of nicotine, caffeine, and menthyl valerate.

An embodiment includes a pharmaceutical composition to inhibit activation of the acetylcholine receptors in the central nervous system of a smoker during use of nicotine-containing products comprising an effective amount of an active ingredient comprising at least one compound selected from the group consisting of camphor, isoborneol, bornyl acetate, isobornyl acetate, mono-bornyl succinate, mono-isobornyl succinate, mono-bornyl formate, and mono-isobornyl formate; wherein the product is free of nicotine, caffeine, and menthyl valerate; and wherein the pharmaceutical composition further comprises a compound suitable for mediating transport across the blood-brain barrier.

Another embodiment includes a method for reducing an individual's desire to engage in smoking comprising preparing a pharmaceutical composition, a portion thereof comprising an effective amount of an active ingredient; and administering the pharmaceutical composition to an individual, wherein the active ingredient comprises at least one compound selected from the group consisting of camphor, isoborneol, bornyl acetate, isobornyl acetate, mono-bornyl succinate, mono-isobornyl succinate, mono-bornyl formate, and mono-isobornyl formate and wherein the product is free of nicotine, caffeine, and menthyl valerate.

An additional embodiment includes a method for decreasing side-effects associated with smoking cessation comprising administering an effective amount of an active ingredient, wherein the active ingredient inhibits at least one of the receptors selected from the group consisting of nicotinic acetylcholine receptors and the TRPA1 channel.

In yet another embodiment, a pharmaceutical composition for decreasing side-effects associated with smoking cessation comprising a therapeutically effective amount of an active ingredient wherein the active ingredient comprises an inhibitor of at least receptor selected from the group consisting of nicotinic acetylcholine receptors and the TRPA1 channel; wherein the product is free of nicotine, caffeine, and menthyl valerate.

BRIEF DESCRIPTION OF THE FIGURES

FIGS. 3A-D shows the antinicotinic effects of camphor.

DETAILED DESCRIPTION

Figure 1A:
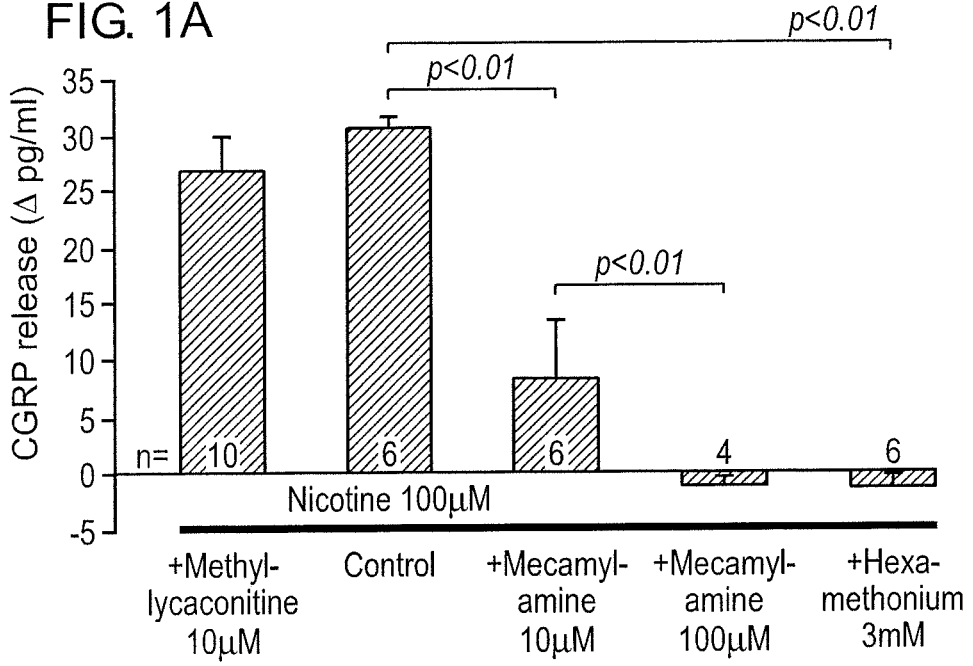
FIGS. 1A-D shows the pharmacology of nicotine on various acetylcholine receptors and the impact of camphor on those receptors.

The present application is directed to a pharmaceutical composition containing at least one active ingredient to support a decrease in the desire to smoke. In one embodiment, the pharmaceutical composition contains an active ingredient that is used in a product for decreasing an individual's desire to smoke. In yet another embodiment, the active ingredient is used in a method of treatment that includes administering to an individual a pharmaceutical composition containing an effective amount of the active ingredient for decreasing an individual's desire to smoke. A further embodiment includes a method of making a pharmaceutical composition containing an effective amount of the active ingredient for decreasing an individual's desire to smoke.

As used herein, the term "edible" denotes the ability of a material or product to be enjoyed and at least partially consumed via the mouth. It includes products such as chewing gum wherein the product is intended for oral use only, not ingestion.

As used herein, the term "portion" denotes an amount of a product that would typically be used by a consumer as an individual serving and/or dose. For example, a portion refers to a single lozenge and/or a single puff from an inhaler.

As used herein, the term "about" when used in conjunction with a stated numerical value or range denotes somewhat more or somewhat less than the stated value or range, to within a range of ±10% of that stated.

As used herein, the singular form "a," "an" and "the" include plural references unless the context clearly dictates otherwise. For example, the term "a cell" includes a plurality of cells, including mixtures thereof.

Active Ingredient

The present application describes the use an active ingredient in pharmaceutical compositions capable of decreasing an individual's desire to smoke. As used herein, when it is said that an active ingredient does not exhibit a sensory effect, it means that an average consumer cannot detect a taste or other sensation (for example, burning, tingling, and/or cooling) arising from the active ingredient when using a portion of the product. In addition, the pharmaceutical composition can be used to alleviate the withdrawal symptoms associated with efforts to stop smoking. In particular, the pharmaceutical composition may be used to alleviate tingling in the extremities, sweating, headaches, cold symptoms, tension and craving.

The pharmaceutical composition may also be employed to decrease an individual's desire to resume smoking after an extended period of nonsmoking by enhancing and/or modifying the sensory experience caused by smoking. In one embodiment, the pharmaceutical composition may be employed prior to smoking to render smoke inhalation unpleasantly bitter, and consequently less enjoyable. Accordingly, the use of the pharmaceutical composition is intended to make smoking less pleasant, and thereby support smoking cessation.

In one embodiment, the active ingredient comprises camphor. Camphor is a terpenoid with the chemical formula $C_{10}H_{16}O$, which has been used to treat respiratory disease indications and to reduce symptoms associated with respiratory diseases. Camphor has also been implicated as having possible anti-viral properties.

It has been reported that the active ingredient camphor can effectively inhibit activation of nerve fibers induced by the nicotinic receptor agonist nicotine in an isolated mouse trachea model. See, e.g., Kichko et al., Acta Physiologica 2007; Volume 189, Supplement 653:P20-L1-03. Camphor has also been reported to inhibit nor-epinephrine release from adrenal gland cells by inhibiting acetylcholine receptors. See, e.g., Park et al., Biochem. Pharmacol. 2002; 61(7):787-793. Thus, camphor has been shown to inhibit activation of nerves in both the peripheral nervous system and the autonomic nervous system. As described herein, the a pharmaceutical composition containing camphor as the active ingredient is administered at therapeutic levels to decrease/inhibit the activation of acetylcholine receptors located on the surface of nerve cells in the central nervous system.

Certain other active ingredients are also expected to provide such inhibition either by acting in the same manner as camphor to inhibit nicotine-mediated activation, and/or by acting as a precursor to camphor or another compound that functions in a similar manner to camphor. Such precursors are expected to be converted to active forms on human consumption, e.g., by metabolic enzymes. Active ingredients appropriate for use include camphor, isoborneol, bornyl acetate, isobornyl acetate, mono-bornyl succinate, mono-isobornyl succinate, mono-bornyl formate, mono-isobornyl formate, derivatives thereof, and/or a combination thereof.

Active ingredients appropriate for use in the pharmaceutical composition may also be selected based on their ability to act on various transient receptor potential (TRP) ion channels. In an embodiment, the pharmaceutical composition includes an active ingredient capable of activating the TRPV1 channel. In another embodiment, the pharmaceutical composition includes an active ingredient that inhibits the TRPA1 channel. In yet another embodiment, the pharmaceutical composition includes an active ingredient that inhibits nicotinic acetylcholine receptors. It will be understood by those skilled in the art that active ingredients appropriate for use in the pharmaceutical composition may function as antagonists to one or more receptors and/or channels and agonists to one or more receptors and/or channels. For example, camphor has been shown to activate the TRPV1 channel in certain tissues, and has been shown to inhibit the TRPA1 channel and nicotinic acetylcholine receptors.

Nicotinic Acetylcholine Receptors

Nicotine, a chemical found in tobacco, produces effects in the body through the activation of neuronal nicotinic acetylcholine receptors. Nicotinic acetylcholine receptors are located on a variety of nerve endings in the peripheral nervous system and play a role in transmission of various sensations to the brain. For example and particularly relevant here, nicotinic acetylcholine receptors may signal a sense of irritation or burning to the brain. Nicotinic acetylcholine receptors are subdivided into two separate classes: $N_1$ and $N_2$. $N_1$ receptors are located at the neuromuscular junction. $N_2$ receptors play a key role in the transmission of cholinergic signals in the autonomic nervous system. These receptors can be found at the autonomic ganglia, the central nervous system and the adrenal medulla. Nicotinic acetylcholine receptors are further subdivided according to the composition of their subunits. In humans, the subunits of nicotinic receptors belong to a 16 gene family.

Nicotine binds to nicotinic acetylcholine receptors, and subsequently triggers the release of neurotransmitters that produce psychoactive effects. In one embodiment, the pharmaceutical composition contains an active ingredient, such as camphor, that when provided at sufficient concentrations, it will target the central nervous system to inhibit acetylcholine receptor activation by nicotine.

Nicotinic acetylcholine receptors exist in various conformational states. Agonists may bind to stabilize an open state. However, acetylcholine receptors can sometimes open with only one bound agonist and, even less frequently, with no agonist bound. Antagonists are also known to bind nicotinic acetylcholine receptors to inhibit their activity. Antagonists may be competitive inhibitors or non-competitive inhibitors. In one embodiment, the pharmaceutical composition contains an active ingredient that acts as an antagonist that acts as a non-competitive inhibitor. In another embodiment, the active ingredient is camphor, which functions as a non-competitive inhibitor of nicotinic acetylcholine receptors in the central nervous system without having a significant impact on nicotine binding.

In some embodiments of the pharmaceutical composition, higher concentrations of the active ingredient are employed to pass through the blood brain barrier. The effects of crossing the blood brain barrier are two-fold—to minimize pleasurable aspects associated with smoking and to increase the bitterness sensed during smoking. In this manner, the taste and positive neurological effects of the cigarettes may be reduced, thereby decreasing a consumer's desire to engage in smoking. It will be appreciated by those skilled in the art that many active ingredients appropriate for use may activate or inhibit other acetylcholine receptors. One such channel of particular import here is the TRPA1 channel. The TRPA1 channel may be activated by a number of compounds, including compounds derived from plants, which elicits acute pain and neurogenic inflammation. As a result, the concentration of the active ingredient may optionally be provided such that the TRPA1 receptor is inhibited. In another embodiment, the active ingredient may be present in a concentration such that the TRPA1 channel is not affected.

Reduced Side Effects of Smoking Withdrawal

Many commercially available smoking cessation products, including CHANTIX, frequently fail to reduce unwanted and unexpected side effects associated with smoking cessation. Common side effects experienced when using such products include nausea, insomnia, headaches, abnormal dreams, gas, changes in taste, constipation, abdominal pain, indigestion, gastroesophageal reflux disease, dry mouth, nightmares, drowsiness, lethargy, fatigue, runny nose and changes in appetite. In addition to side effects associated with smoking cessation, currently available products may also directly cause similar symptoms. The pharmaceutical composition described herein aims to reduce the negative side effects associated with smoking cessation. Thus, pharmaceutical compositions utilize active ingredients that are known to produce minimal side-effects when administered to an individual, and are also capable of reducing the negative side effects produced during smoking withdrawal.

In one embodiment, the active ingredient is camphor. Side effects and potential toxicity of camphor are well known and documented. Camphor is readily absorbed through the skin and produces a feeling of cooling similar to that of menthol, and acts as a slight local anesthetic and antimicrobial substance. There are anti-itch gels and cooling gels with camphor as the active ingredient. Camphor is an active ingredient (along with menthol) in vapor-steam products, such as VICKS VAPORUB. Although touted as a cough suppressant, it has no effects on respiratory tract function. Due to its well-known toxicity profile, camphor is an ideal active ingredient for use with the present pharmaceutical composition.

Treatment of the Central Nervous System

In one embodiment, the pharmaceutical composition is targeted directly to the central nervous system. In order to effectively act on the central nervous system, the composition may include additional ingredients suitable to mediate transport across the blood-brain barrier.

Mechanisms for drug targeting in the brain may include going either "through" or "behind" the blood-brain barrier. In some embodiments, the pharmaceutical composition may be designed to mediate transport across the blood-brain barrier by osmotic means; biochemically by the use of vasoactive substances such as bradykinin; or even by localized exposure to high-intensity focused ultrasound. Other methods that may be used to mediate transport of the pharmaceutical composition across the blood-brain barrier include the use of endogenous transport systems, including carrier-mediated transporters such as glucose and amino acid carriers; receptor-mediated transcytosis for insulin or transferrin; and the blocking of active efflux transporters such as p-glycoprotein. Methods for drug delivery behind the blood-brain barrier may include intracerebral implantation (such as with needles) and convection-enhanced distribution.

Forms of the Active Ingredient

The active ingredient may be provided in a variety of forms. In an embodiment, the active ingredient is provided in the form of an edible product. An edible product can take the form of a tablet, lozenge, stick, chewable gum, spongy material, foam, cream, pellet, fiber, pill, capsule, pouched products, or combinations of these. Other examples of edible products include such chewable or non-chewable edible forms as tablets, gums, chocolates, flavored sponges, flavor strips, and the like. The product may be administered orally or as a sprayable composition. The product may be prepared as a vapor. The product preferably lacks nicotine, caffeine, and menthyl valerate. Preferably, the product is also free of other active ingredients apart from the one or more active ingredients already disclosed, such as, for example, quinine, and/or ingredients that are classified and/or regulated as drugs.

Because the pharmaceutical composition is intended to cross the blood-brain barrier to act on the central nervous system higher doses of active ingredient are used relative to compositions intended to act only on the peripheral nervous system. In an embodiment the active ingredient forms part of a pharmaceutical formulation where the active ingredient is present in an amount greater than about 9 milligrams. In another embodiment the active ingredient forms part of a pharmaceutical formulation where the active ingredient is present in an amount from about 9-24 milligrams.

Pharmaceutical compositions appropriate for use may be formulated as single daily dose treatment regimen. In yet another embodiment, the composition is formulated as a multiple daily dose treatment regimen.

In the case of topical treatments, dosage concentrations of the active ingredient fall within a range capable of acting on the nicotinic acetylcholine receptors without activating the TRPA1 channel. This treatment regime only applies to the periphery. As a result, treatment using pharmaceutical compositions described herein is unlikely to exhibit reverse effects beyond a certain dose. However, those skilled in the art will appreciate that one must be cognizant of the possibility of overdose. When administered topically, the dose dependent effect on the central nervous system is likely to be 50-100 times as much as that used for local treatments.

In another embodiment, the pharmaceutical composition is encapsulated for release upon contact with saliva. Camphor and beta-cyclodextrin readily form an inclusion complex wherein the former is stabilized within the cavity of the host cyclodextrin. To encapsulate the camphor, beta-cyclodextrin can be dissolved in a minimum amount of hot water and the camphor dissolved in minimum amount of alcohol, then added to the cyclodextrin. The mixture is then heated to no more than 75 degrees C. until all solids have dissolved. Upon cooling to 4 degrees C., precipitated solid encapsulated camphor can be recovered as a white solid. It is expected that the other active ingredients could be similarly encapsulated. Materials other than cyclodextrin can also be used to encapsulate the pharmaceutical composition. Encapsulation is expected to prevent loss of the active ingredient. This is particularly useful in embodiments that include camphor or similar related active agents, which are somewhat volatile, thereby increasing shelf stability and consistency of the product incorporating the encapsulated active ingredient.

It is contemplated that oral supplementation may be provided in a solid oral dosage form, such as in a capsule form, for treatment requirements when taken by a human, animal, and the like. Oral dosage forms encompass tablets and capsules. Other dosage forms include suitable solutions for administration topically, parenterally, orally, and compositions which can be administered buccally or sublingually.

The pharmaceutical composition may also be formulated as a vapor. In one embodiment, the pharmaceutical composition is a formulation including camphor crystals that can be vaporized. Methods for use of such a pharmaceutical composition require that the crystals of the pharmaceutical composition be vaporized for a period of time, during which the individual will inhale the vapor. The period of exposure to the vaporized pharmaceutical composition may vary. In one embodiment, the individual will inhale the vapor for a period of at least twenty minutes. In another embodiment, the individual will inhale the vapor for a period of at least 30 minutes. When the pharmaceutical composition is inhaled as a vapor, it may be administered as a single daily dose treatment regimen or as a multiple daily dose treatment regimen.

In another embodiment, the pharmaceutical composition is provided in a spray form, i.e., a sprayable product that permits spraying of the active ingredient (together with an optional vehicle) into the mouth. If the product is to be administered in a spray form, the packaging preferably comprises an inhaler, such as a metered inhaler.

While the foregoing has been described in detail with reference to specific embodiments thereof, it will be apparent to one skilled in the art that various changes and modifications may be made, and equivalents thereof employed, without departing from the scope of the claims.

It is to be understood that the claims of this application is not limited to particular embodiments described. It is also to be understood that the terminology used herein is for the purpose of describing particular embodiments only, and is not intended to be limiting, since the scope of the present application will be limited only by the appended claims.

Unless defined otherwise, all technical and scientific terms used herein have the same meaning as commonly understood by one of ordinary skill in the art. Although any methods and materials similar or equivalent to those described herein can also be used in the practice or testing of exemplary embodiments, specific preferred methods and materials are now described.

EXAMPLES

Example 1—Mouse Trachea Example

Figure 1B:
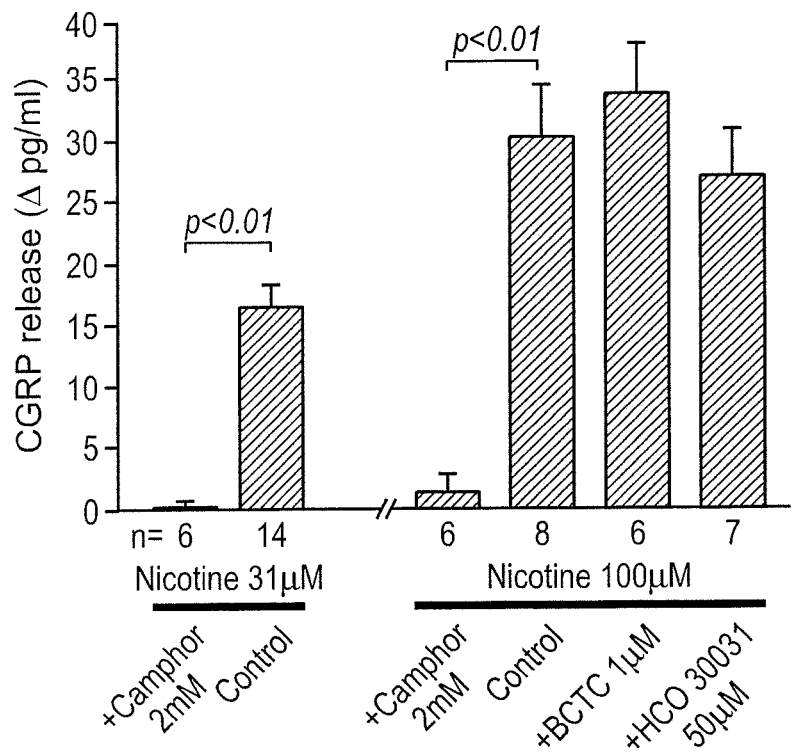
Figure 1C:
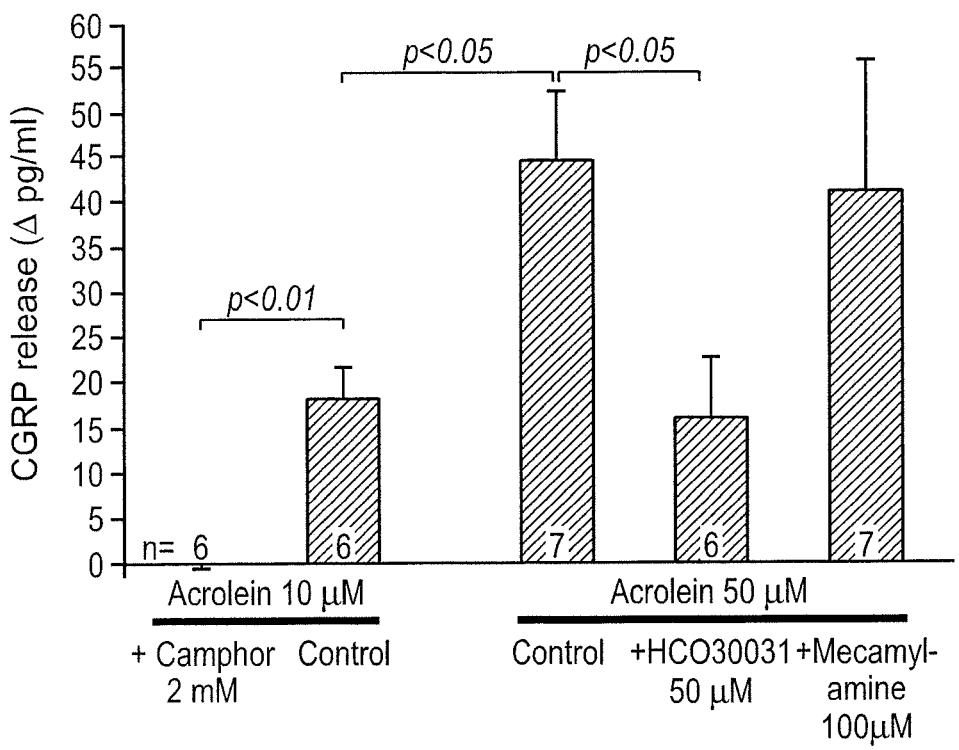
Figure 1D:
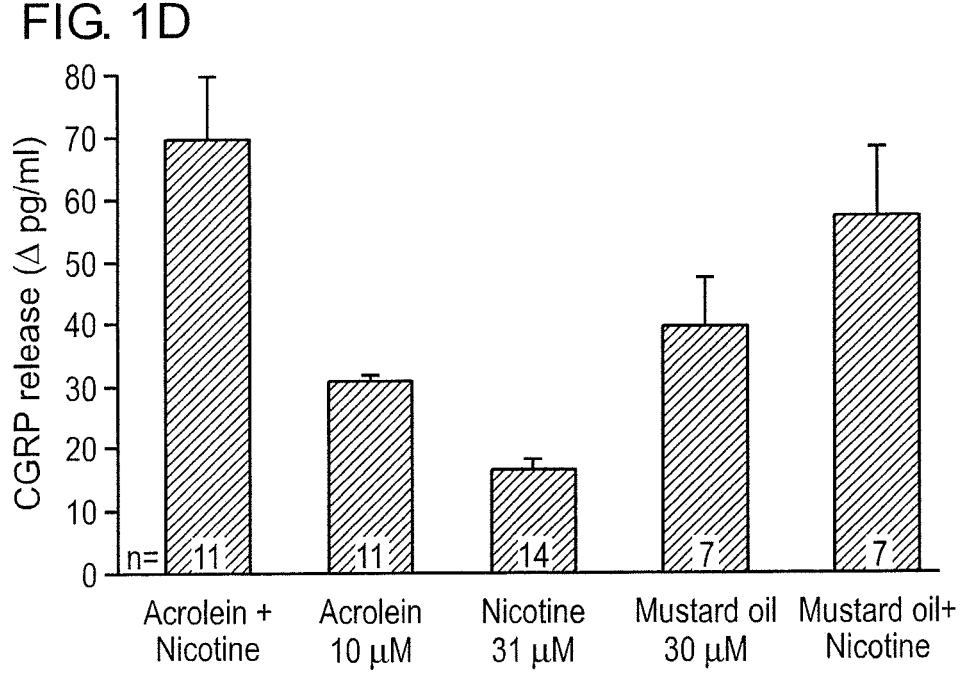

It has been shown that nicotine can induce the release of calcitonin gene-related peptide (CGRP) in the trachea of mice by acting on acetylcholine receptors (FIG. 1a). CGRP is a sensory biomarker of neurons that mediate information to the brain. CGRP release can be detected in vitro using whole trachea tissue by exposing the tissue to a stimulatory compound. A standard ELISA assay may then be used to measure the release of CGRP. The active ingredient was tested using a mouse trachea model. As shown in FIG. 1 b, the addition of camphor to trachea samples exposed to nicotine released less CGRP compared to samples exposed to nicotine alone. To demonstrate that the effects are specific to the nAChR receptor, trachea samples were exposed to combinations of nicotine and inhibitors of the TRPV1 channel (BCTC) and the TRPA1 channel (HC030031). (FIG. 1b). Tissue samples exposed to nicotine and BCTC or nicotine and HC030031 did not show any significant reduction in CGRP release relative to samples exposed to nicotine alone. (FIG. 1b). Other activators of acetylcholine receptors have also been found to stimulate the release of CGRP in trachea tissue. For example, acrolein, a known activator of the TRPA1 channel, has been shown to cause CGRP release at various concentrations. (FIG. 1c). Similar to the results observed with nicotine, the combination of acrolein and camphor resulted in a decrease in CGRP release in trachea samples, demonstrating that camphor can inhibit activation of both nAChR and the TRPA1 channel. (FIG. 1c). Additionally, when acrolein and HCO30031 were used in combination, CGRP release was also reduced. (FIG. 1c). Finally, as shown in FIG. 1d, when multiple acetylcholine receptors are activated, CGRP release is enhanced. Thus, camphor is an effective inhibitor of nicotinic acetylcholine receptors when administered in low concentrations in the trachea.

Figure 2A:
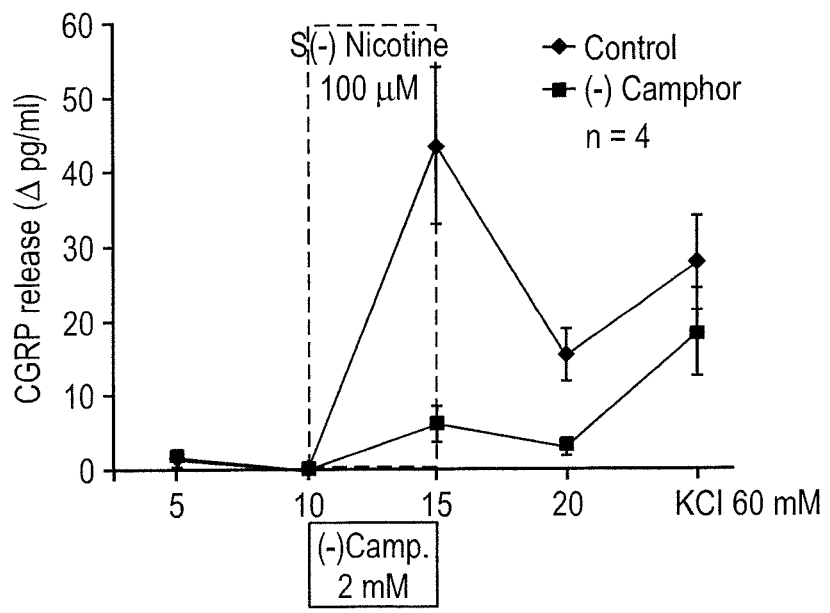
FIGS. 2A-B shows the effect of camphor enantiomers on the nicotinic response using a mouse trachea model.
Figure 2B:
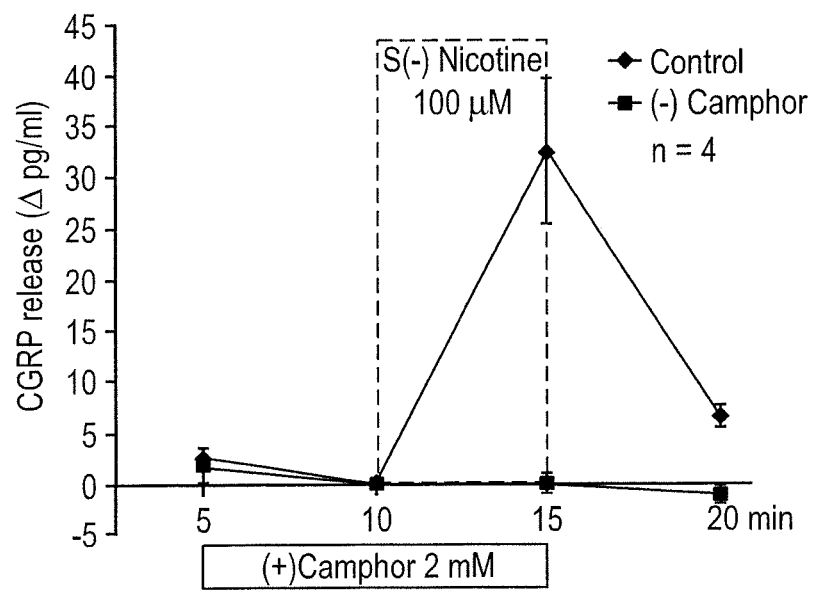

In order to determine whether a specific enantiomer of the active ingredient show greater efficacy, time course experiments were conducted in which trachea tissue samples were pretreated with nicotine and exposed to either the (−) or (+) enantiomer of camphor. (FIG. 2). As can be seen, both camphor enantiomers are effective at abolishing the maximal nicotinic response.

Figure 3A:
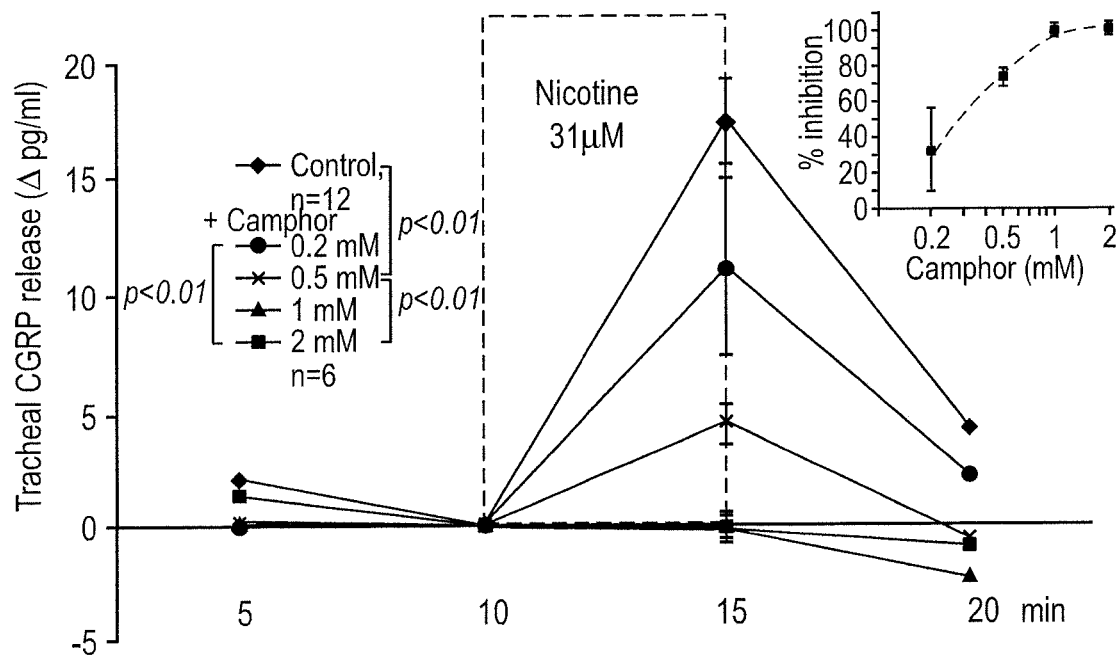
Figure 3B:
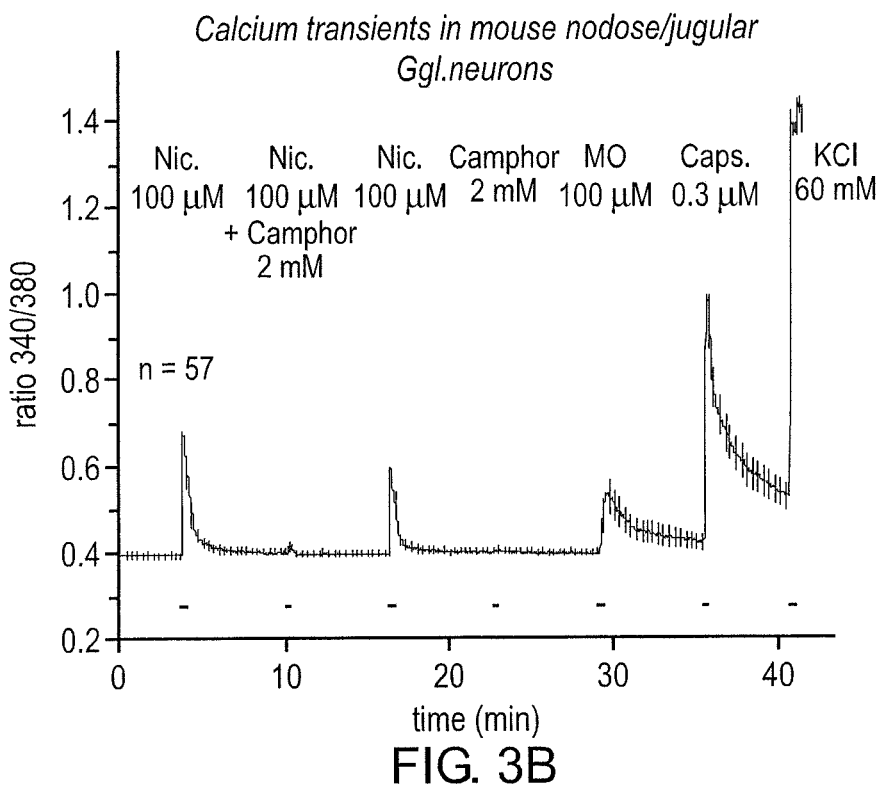

The anti-nicotinic effects of camphor have been shown to be dose dependent. (FIG. 3a). When mouse trachea samples were exposed to nicotine and various concentrations of camphor, CGRP release was decreased as the concentration of camphor was increased. Calcium-imaging experiments were performed on mouse nodose/jugular Ggl neurons with images captures at 340 and 380 nm over time. (FIG. 3b). As can be seen, nicotine stimulated calcium influx in Ggl neurons when give alone, but not when given in combination with camphor. (FIG. 3b). The ability of camphor to inhibit tracheal release of CGRP through acetylcholine receptors is not specific to nicotine. Tracheal tissue samples exposed to epibatidine, a known activator of the nAChR receptor, also resulted in increased release of CGRP. (FIG. 3c). The release of CGRP could be inhibited by camphor as well as another nAChR inhibitor, Mecamylanine. (FIG. 3c). In addition, camphor effectively inhibited CGRP release in the absence of the TRPA1 channel. (FIG. 3d). Thus, the anti-nicotinic effects of camphor can be modified in a dose-dependent manner.

Figure 4:
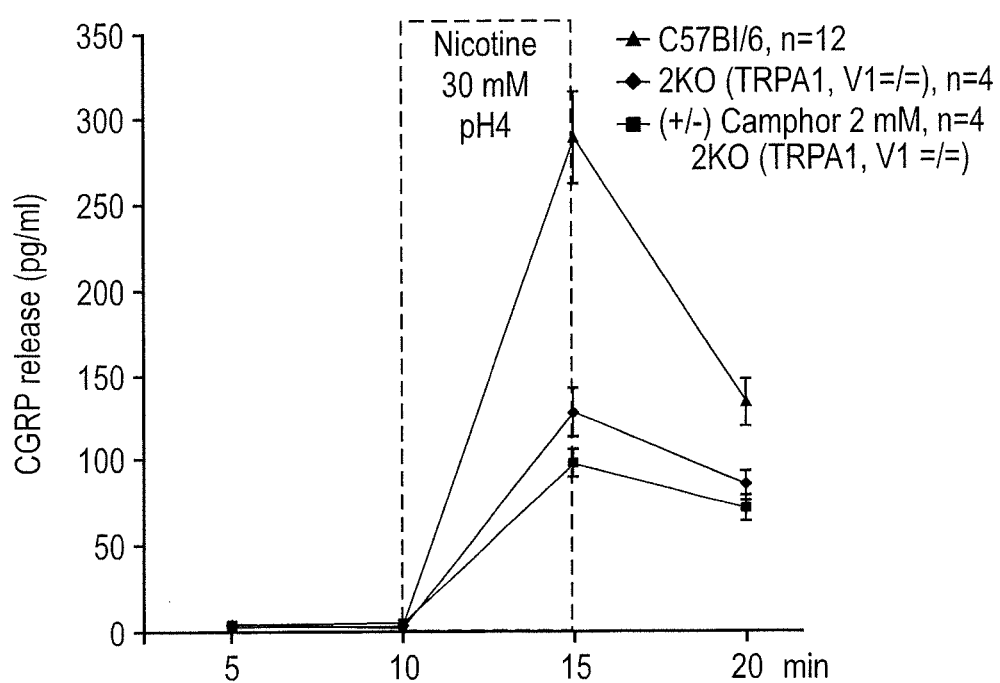
FIG. 4 shows camphor treatment in TRPA1/V1 double-knockout mice.

Tracheal samples from TRPA1 knockout mice showed a marked reduction in CGRP release following exposure to epibatidine and camphor compared to samples exposed to epibatidine alone. However, camphor was not shown to alter the nicotine response in buccal mucosa tissue samples in TRPA1/TRPV1 double knockouts. Buccal mucosa samples obtained from normal C57Bl/6 mice exposed to nicotine released increased amounts of CGRP. (FIG. 4). Mice lacking both the TRPA1 and TRPV1 channels did not respond to nicotine exposure by releasing similar amounts of CGRP relative to normal mice. (FIG. 4). In addition, the TRPA1/TRPV1 double knockouts did not show a significant change in CGRP release when exposed to both nicotine and camphor. (FIG. 4).

Figure 5A:
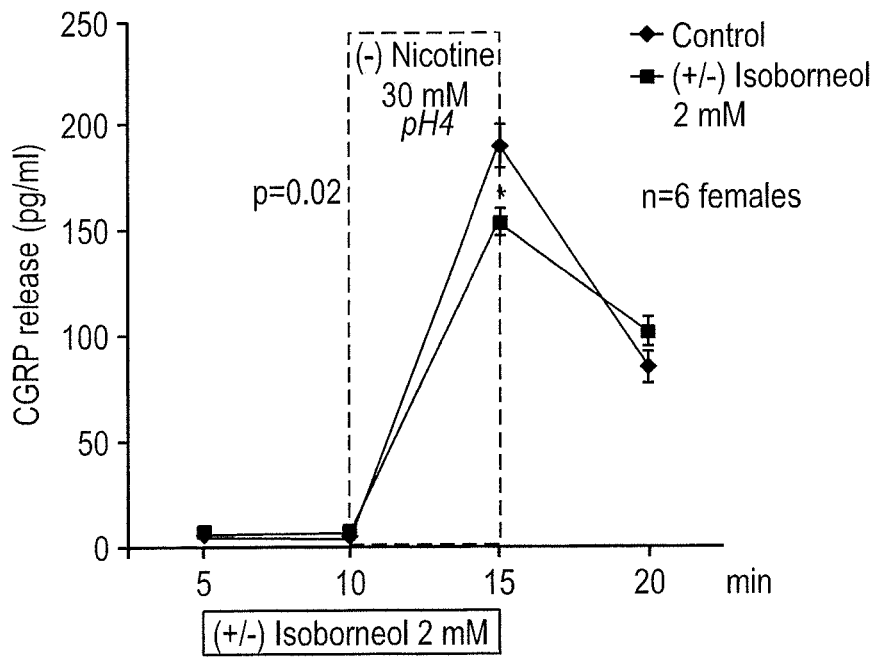
FIGS. 5A-B shows the effect of (+/−) isoborneol treatment on the nicotinic response.
Figure 5B:
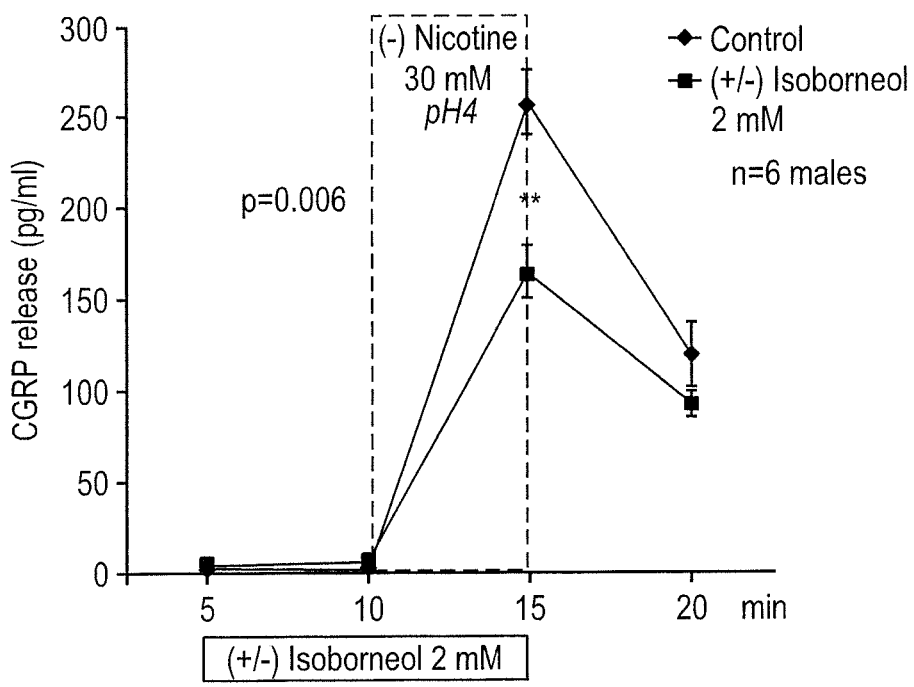

Active ingredients appropriate for use in embodiments described herein may also include isoborneol. To show the efficacy of isoborneol, time course experiments were performed in which buccal mucosa tissue samples were exposed to nicotine alone or nicotine followed by exposure to camphor. Exposure to nicotine resulted in increased release of CGRP (FIGS. 5a and 5b). However, CGRP release was significantly lower in the samples that were exposed to camphor following the nicotine exposure. (FIGS. 5a and 5b). The gender of the mice did not affect the outcome of the experiments; however, samples obtained from male mice showed stronger inhibition. Therefore, in some embodiments, inhibitors of the nicotinic acetylcholine receptors or the TRPA1 channel may be administered both before and after nicotine consumption.

Figure 6:
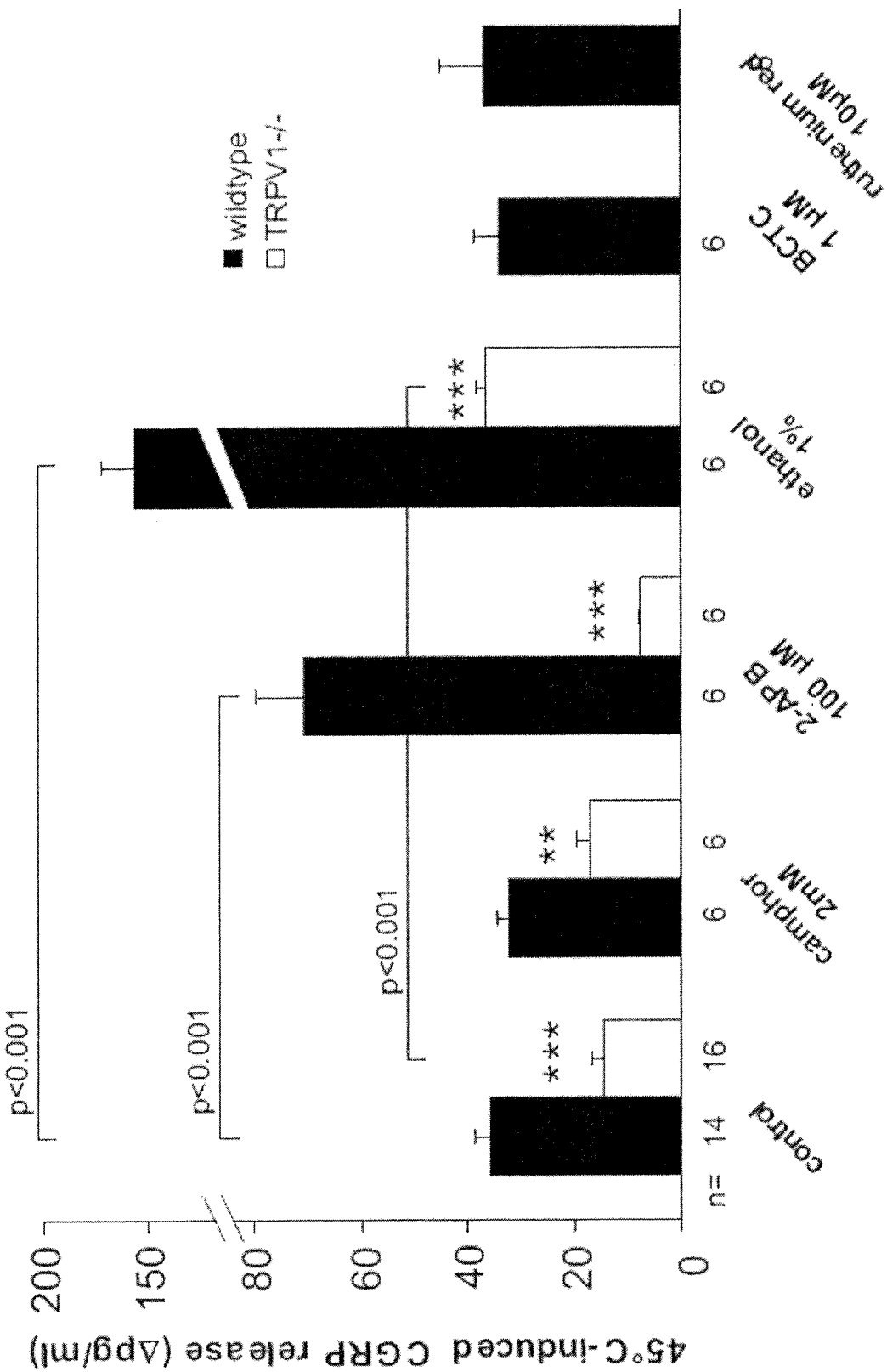
FIG. 6 shows the sensitization to heat is TRPV1-dependent.

In order to show that camphor does not inhibit TRPV1 channel signaling, tracheal samples were heated to 45° C. to induce the release of CGRP. Tracheal tissue samples exposed to camphor and heat treatment released comparable levels of CGRP relative to normal samples. (FIG. 6). Similarly, tracheal samples obtained from TRPV1 knockout mice exposed to camphor and heat treatment released comparable levels of CGRP relative to normal samples. (FIG. 6). 2-APB and ethanol, both activators of the TRPV1 channel, were both shown to increase CGRP release in heat treated tracheal samples. (FIG. 6). In addition, TRPV1 knockout samples treated with ethanol also showed an increase in CGRP release relative to untreated TRPV1 knockouts, but the CGRP release in these samples was 5-fold less than that observed in ethanol-treated normal samples. (FIG. 6). Thus, camphor is not an inhibitor of the TRPV1 channel.

Figure 7A:
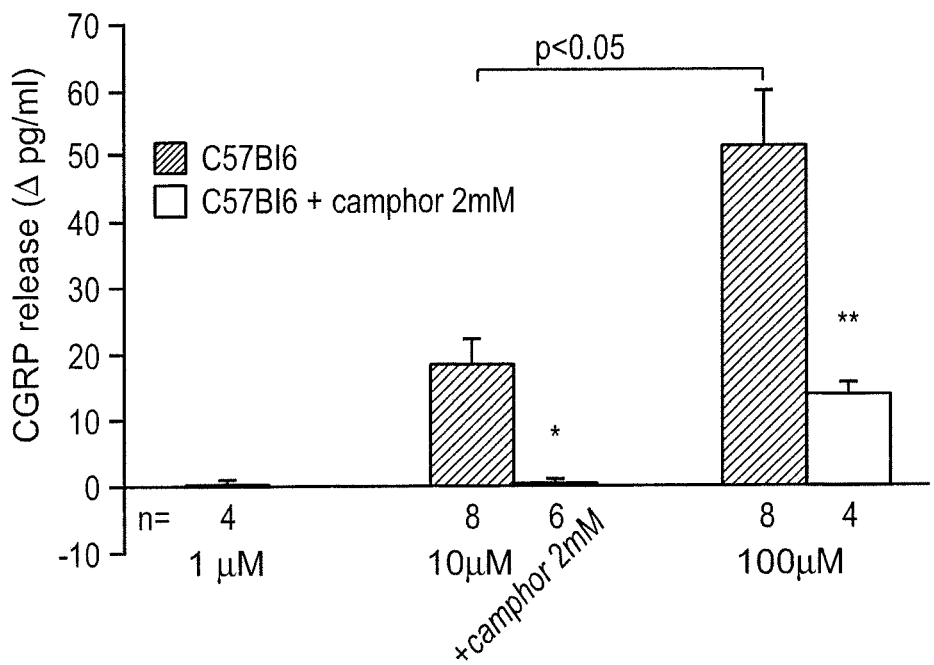
FIGS. 7A-B shows the ability to overcome TRPA1 channel inhibition by camphor is dose dependent.
Figure 7B:
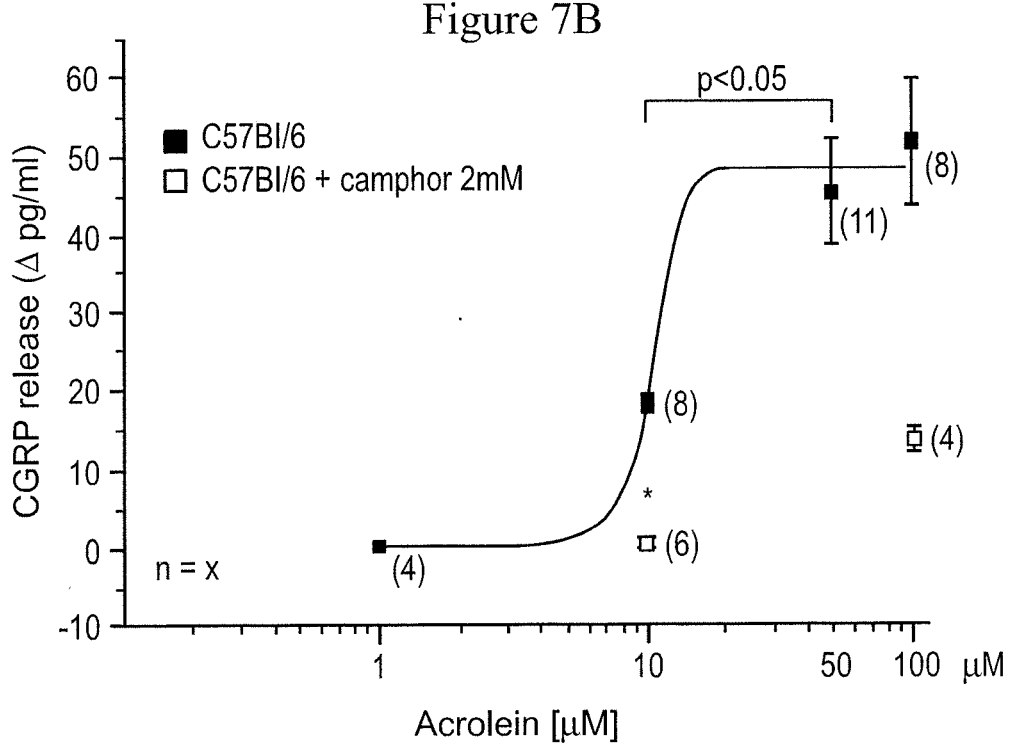

CGRP release stimulated by acetylcholine receptors is dose-dependent. Tracheal tissue samples exposed to acrolein released increased amounts of CGRP when exposed to higher concentrations of acrolein. (FIG. 7). When tracheal tissue samples were exposed to camphor in combination with acrolein exposure, they showed a marked reduction in CGRP release. (FIG. 7). As acrolein concentration was increased, CGRP release was increased in camphor treated samples; however, the camphor treated samples still released significantly lower levels of CGRP relative to samples exposed only to acrolein at the same concentration. (FIG. 7).

Figure 8A:
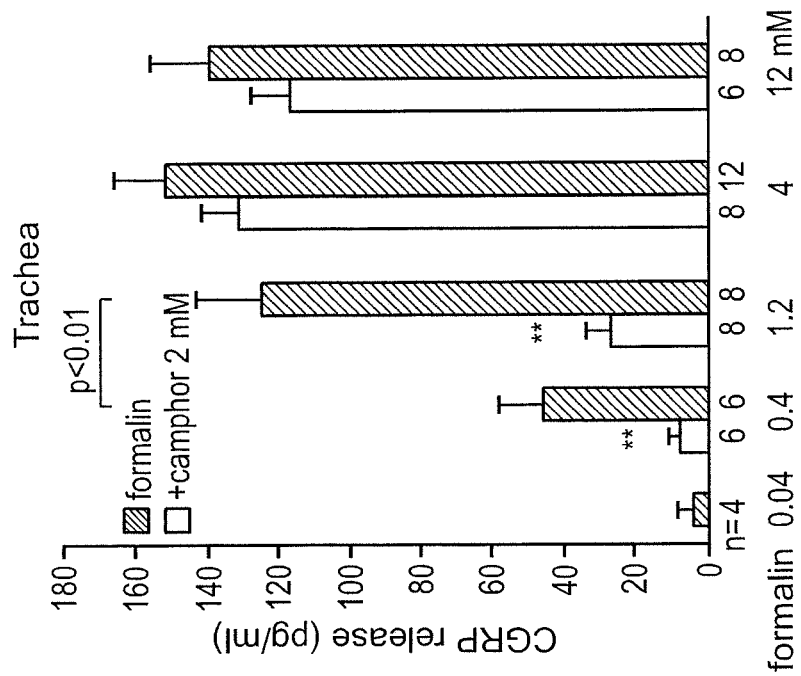
FIGS. 8A-B shows camphor mediated inhibition of the TRPA1 channel may be overcome by increased concentrations of a TRPA1 agonist.
Figure 8B:
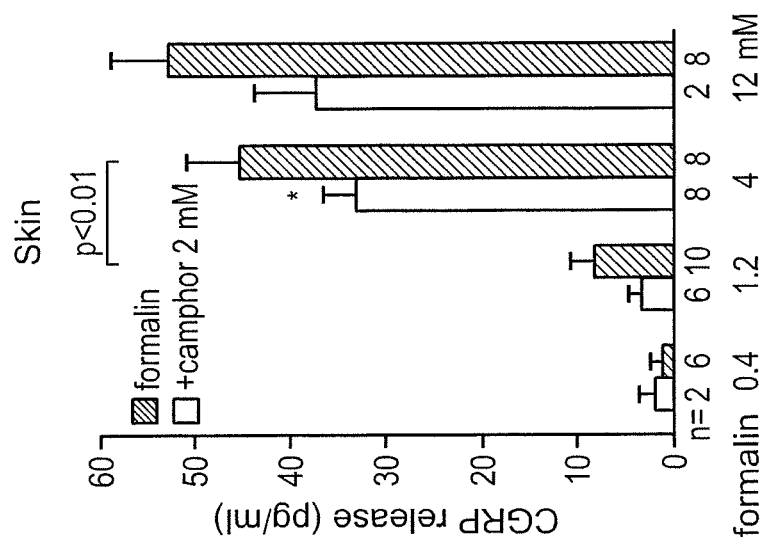
Figure 9:
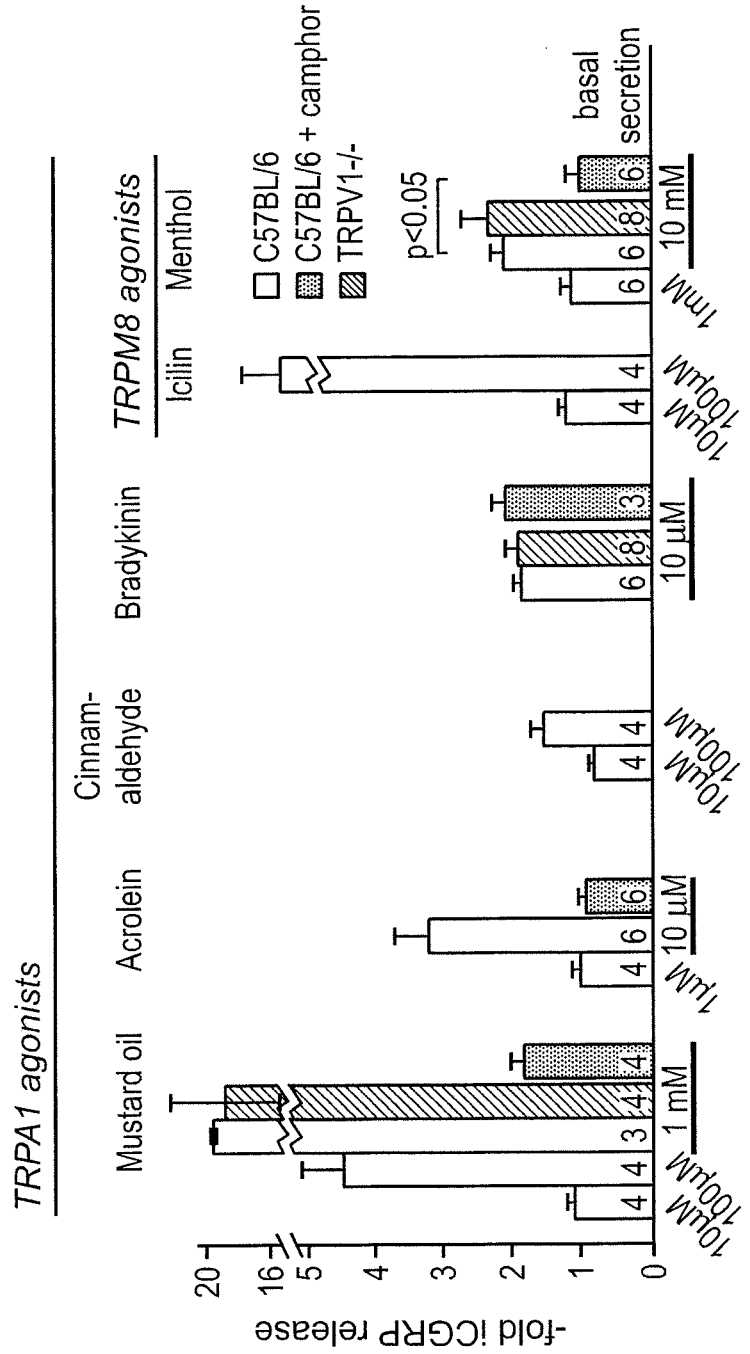
FIG. 9 shows the impact of camphor on the TRPA1 and TRPM8 channels in the presence of receptor agonists.

Similar dosing experiments were performed using formalin, a TRPA1 channel antagonist. There, camphor exposure resulted in a decrease in formalin-stimulated GCRP release in both skin and tracheal tissue samples. (FIG. 8). However, in both tissue samples, the effects of camphor could be overcome at high formalin concentrations. Thus, in some embodiments, active ingredients may be used that inhibit both the nicotinic acetylcholine receptors and the TRPA1 channel. Several TRPA1 channel irritants have been shown to stimulate the release of immunoreactive CGRP (iCGRP) in tracheal tissue samples. (FIG. 9). The addition of camphor to these samples has been shown to reduce the TRPA1 channel mediated release of iCGRP. (FIG. 9).

Figure 10A:
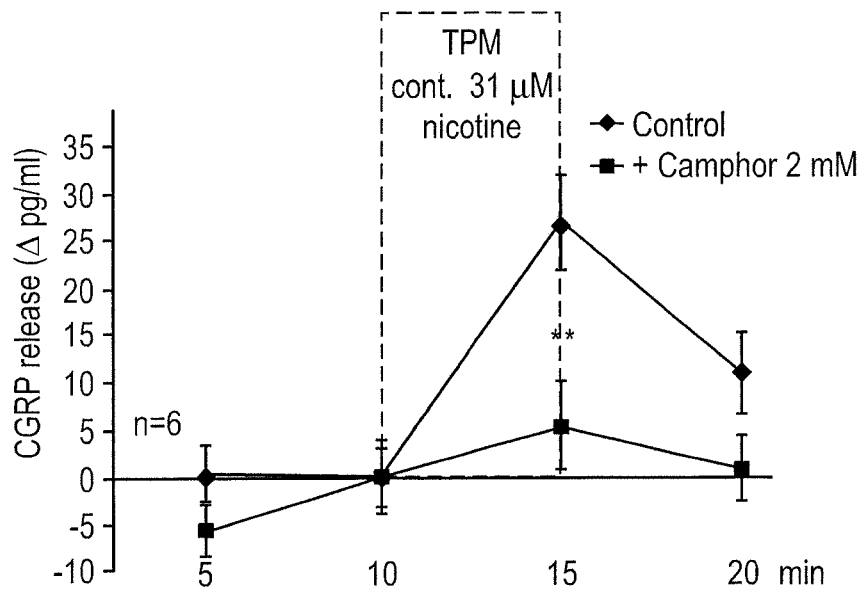
FIGS. 10A-B shows camphor inhibition of nicotine and TPM responses.
Figure 10B:
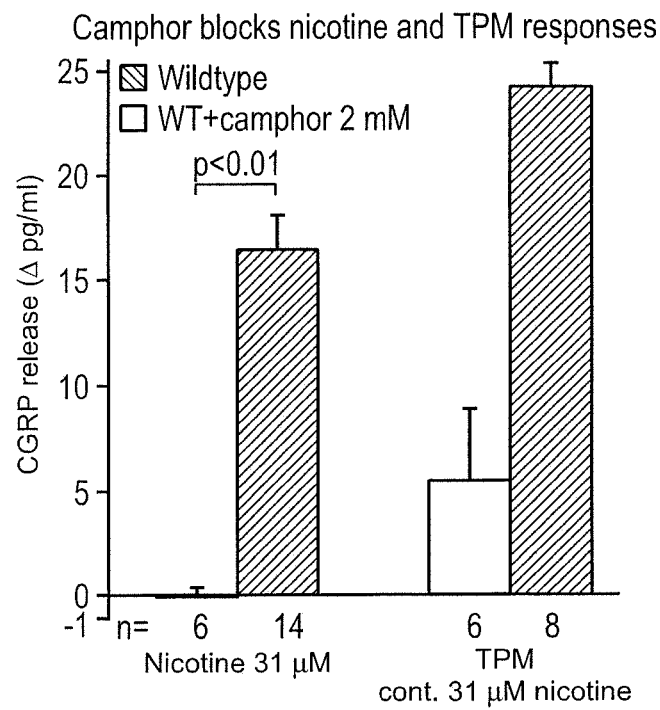

To assess the potential of camphor on GCRP release stimulated by cigarette smoking, tracheal tissue samples were exposed to total particulate matter (TPM) containing the same amount of nicotine as in the nicotine alone experiment. Exposure to TPM+nicotine resulted in the release of GCRP. (FIG. 10). This release of GCRP was largely blocked when the samples were exposed to camphor and TPM exposure. (FIG. 10). The results observed in the TPM experiments are similar to those seen in experiments in which nicotine is used alone. (FIG. 10).

It is to be understood that, while the systems, products, compositions of matter, and methods have been described herein in conjunction with a number of different embodiments, the foregoing description of the various embodiments is intended to illustrate and not limit the scope of the claimed systems, products, compositions of matter, and methods. Other embodiments, advantages, and modifications are within the scope of the following claims. All publications cited herein are incorporated herein by reference in their entirety for all purposes.

What is claimed is:

1. A smoking cessation treatment, comprising administering to the trachea and/or buccal mucosa of a human subject an effective amount of a product comprising an effective amount of an active ingredient consisting of at least one compound selected from the group consisting of bornyl acetate, isobornyl acetate, mono-bornyl succinate, mono-isobornyl succinate, mono-bornyl formate, and mono-isobornyl formate; wherein the product is free of nicotine, caffeine, and menthyl valerate, wherein the human is a smoker, and wherein the active ingredient is present in an amount from about 9 milligrams to about 24 milligrams.

2. A method for reducing an individual's desire to engage in smoking comprising: preparing a pharmaceutical composition, a portion thereof comprising an effective amount of an active ingredient; and administering the pharmaceutical composition to the trachea and/or buccal mucosa of an individual, wherein the active ingredient consists essentially of at least one compound selected from the group consisting of bornyl acetate, isobornyl acetate, mono-bornyl succinate, mono-isobornyl succinate, mono-bornyl formate, and mono-isobornyl formate wherein the pharmaceutical composition is free of nicotine, caffeine, and menthyl valerate, and wherein the active ingredient is present in an amount from about 9 milligrams to about 24 milligrams.

3. The method of claim 2, wherein the pharmaceutical composition is administered to an individual by at least one route selected from the group consisting of topically, orally, and by inhalation.

4. The method of claim 2, wherein the method further comprises preparing the pharmaceutical composition as a vapor and treating an individual who is a smoker through inhalation.

5. The method of claim 2, wherein the pharmaceutical composition is administered as a multiple daily dose regimen.

* * * * *